(12) United States Patent
Sarkis et al.

(10) Patent No.: US 7,438,223 B2
(45) Date of Patent: Oct. 21, 2008

(54) RECHARGEABLE SMART CARD BLOOD PRESSURE RECORDING METHOD AND APPARATUS

(75) Inventors: Fred Sarkis, Rochester, NY (US); Joseph O. Sarkis, Vancouver (CA); Lisa Goodwin, Penfield, NY (US)

(73) Assignee: Pharma-Smart LLC, Rochester, NY (US)

( * ) Notice: Subject to any disclaimer, the term of this patent is extended or adjusted under 35 U.S.C. 154(b) by 0 days.

(21) Appl. No.: 11/502,738

(22) Filed: Aug. 11, 2006

(65) Prior Publication Data

US 2007/0057041 A1    Mar. 15, 2007

Related U.S. Application Data

(60) Provisional application No. 60/708,125, filed on Aug. 12, 2005.

(51) Int. Cl.
    *G06K 5/00* (2006.01)
(52) U.S. Cl. .................. 235/380; 235/492; 235/385; 235/451
(58) Field of Classification Search .................. 235/492, 235/380, 385, 449, 451, 454, 487; 600/319
See application file for complete search history.

(56) References Cited

U.S. PATENT DOCUMENTS

| 5,307,263 A * | 4/1994 | Brown .......................... 600/301 |
| 5,827,179 A * | 10/1998 | Lichter et al. ................ 600/300 |
| 6,283,369 B1 * | 9/2001 | Kurokawa et al. ........... 235/380 |
| 6,378,073 B1 * | 4/2002 | Davis et al. ..................... 726/1 |
| 6,524,240 B1 * | 2/2003 | Thede .......................... 600/300 |
| 6,563,596 B1 * | 5/2003 | Narushima ................. 358/1.14 |
| 6,712,762 B1 * | 3/2004 | Lichter et al. ................ 600/300 |
| 2004/0167381 A1 * | 8/2004 | Lichter et al. ................ 600/300 |

* cited by examiner

*Primary Examiner*—Seung H Lee
(74) *Attorney, Agent, or Firm*—Hiscock & Barclay, LLP (57) ABSTRACT

Enabling the providers of automated blood pressure readings, such as pharmacies, corporate work sites, health clubs and other customers, to charge a fee for the long-term use of a memory card to record non-invasive physiological test data and make the data available for health consultations. In an automated blood pressure system with one or more memory-card interface devices, a custom-formatted end-user memory card keeps track of the user's non-invasive physiological test data, and a recharge memory card controls the provider's recharging of the end-user memory card after the end-user memory card expires. The contents of the recharge memory card are updated in order to track its use by the provider of the readings.

42 Claims, 7 Drawing Sheets

RECHARGEABLE SMART CARD BLOOD PRESSURE RECORDING METHOD AND APPARATUS

CROSS-REFERENCE TO RELATED APPLICATIONS

This application claims the benefit of the priority date of U.S. Provisional patent application Ser. No. 60/708,125 filed Aug. 12, 2005.

BACKGROUND AND FIELD OF THE INVENTION

The invention relates to the use of "smart card" storage of data, and more specifically to the use of "smart cards" to store medical test result information.

SUMMARY

Automated blood pressure (ABP) machines and other types of non-invasive medical self-monitoring equipment, e.g., automated glucose monitors, cholesterol monitors, blood oxygen monitors are either purchased or leased by pharmacies, corporate work sites, health clubs and other customers. For the purpose of this discussion, these customers will be referred to as "Locations".

The Locations provide ABP and other medical self-monitoring machines as a service to their customers, employees, members, etc. For the purpose of this discussion, we will refer to these customers, employees, and members using the ABP or other medical self-monitoring machines as the "End User". Such Locations often offer the End User the option to use a memory card or a Smart Card to record and track their blood pressure history over time.

As used in this patent, the term "memory card" includes any device that is generally the size of credit card (2"×3.25") with power, ground, input and output ports or terminals and an array of memory cells arranged in rows and columns. Such memory cells are typically made of flash memory which are static memory devices that retain their information when electrical energy to the card is removed. Smart Cards include memory arrays of flash memory cells and have a microprocessor or other control or logic circuitry. One purpose of the microprocessor or other circuitry is to provide security for the data on the card. Such Smart Cards have encryption and decryption keys or stored programs that secure the card from unwanted access.

Each time the End User uses the memory card or Smart Card in the machine, the blood pressure reading, pulse rate, and the date of the measurement are recorded on the card. The ABP machine then prints out a history of the End User's most recent results (as many as 10 results), and provides a calculated average blood pressure and pulse rate for the End User.

Similar monitoring, data collection, data compilation, and data presentation opportunities exist for other forms of medical self-monitoring equipment. A printed history of the End User's most recent results for any such monitoring process is important as it provides the End User with information to share with physicians, pharmacists, and other health care professionals. Recorded ABP information assists the health care professional in evaluating the End User's blood pressure history and the effectiveness of any End User hypertension control program. Recorded glucose levels, cholesterol levels, blood oxygen levels, and other records of medical monitoring for the End User can likewise assist health care professionals in their care of that End User.

The invention enables the providers of automated blood pressure readings and other non-invasive physiological test data, such as pharmacies, corporate work sites, health clubs and other customers, to charge an annual fee for the use of a memory card or Smart Card to record the non-invasive physiological test data and make the data available for health consultations. The invention's software, installed in an automated blood pressure system or other medical self-monitoring system with one or more memory card or Smart Card interface devices, uses a custom-formatted end-user memory card for keeping track of the user's non-invasive physiological test data and the dates these readings were taken. The software also uses a recharge memory card for controlling the provider's recharging of the end-user memory card. The invention's processing reactivates the end-user memory card or Smart Card after it expires, and updates the contents of the recharge memory card in order to track the number of recharges provided.

The invention's apparatus and methods also apply to non-medical systems for recording readings and verifying usability.

DETAILED DESCRIPTION OF THE INVENTION

In its basic embodiment, the invention is both an apparatus and a process, developed initially for the PharmaSmart Model PS-2000 blood pressure machine and similar machines made by others. The PS-2000 is equipped to use blood pressure Smart Cards to store blood pressure readings for the End User. It is likely that millions of these blood pressure Smart Cards will eventually be in circulation in North America and in other parts of the world. The invention provides the option for Locations to: 1) generate additional revenues by charging the End User an annual fee for use of the Smart Card, and 2) provide End User with at least one annual blood pressure consultation.

The use of the invention is as follows. The Location issues a Smart Card to the End User. The first time the End User uses the Smart Card in the ABP machine, it electronically "stamps" a recharge date onto the Smart Card. The recharge date is a fixed or variable date, but preferably is one (1) year from the date of first use in the machine. This means the End User has a full year of use of the Smart Card before it will require a recharge. If the card is not recharged by the recharge date, it will no longer work in the ABP machine.

At any time, the Location may purchase recharge credits directly from manufacturer of the ABP machine. These credits are loaded onto a unique "Recharge Smart Card", and shipped directly to the Location. Upon the End User's request, the Location personnel can use the Recharge Smart Card to recharge the End User's card for an additional year. In order to do this the Location personnel must have both the Recharge Smart Card and the End User Smart Card in hand. They then simply insert the Recharge Smart Card into the ABP machine and follow the instructions provided on the machine's display. Once completed, an updated recharge date is electronically "stamped" onto the End User Smart Card providing another full year of use of the Smart Card. Each time the Location personnel recharges an End User Smart Card, the Recharge Smart Card is debited one (1) recharge credit. Once all of the recharge credits are used, the Location personnel discards the Recharge Smart Card and, as required, may order an additional Recharge Smart Card from the ABP machine manufacturer.

The ABP machine manufacturer may charge Locations a fee for each recharge credit they order, and the Location, in turn, can charge the End User an annual fee for the User Smart Card.

Figure 1A:
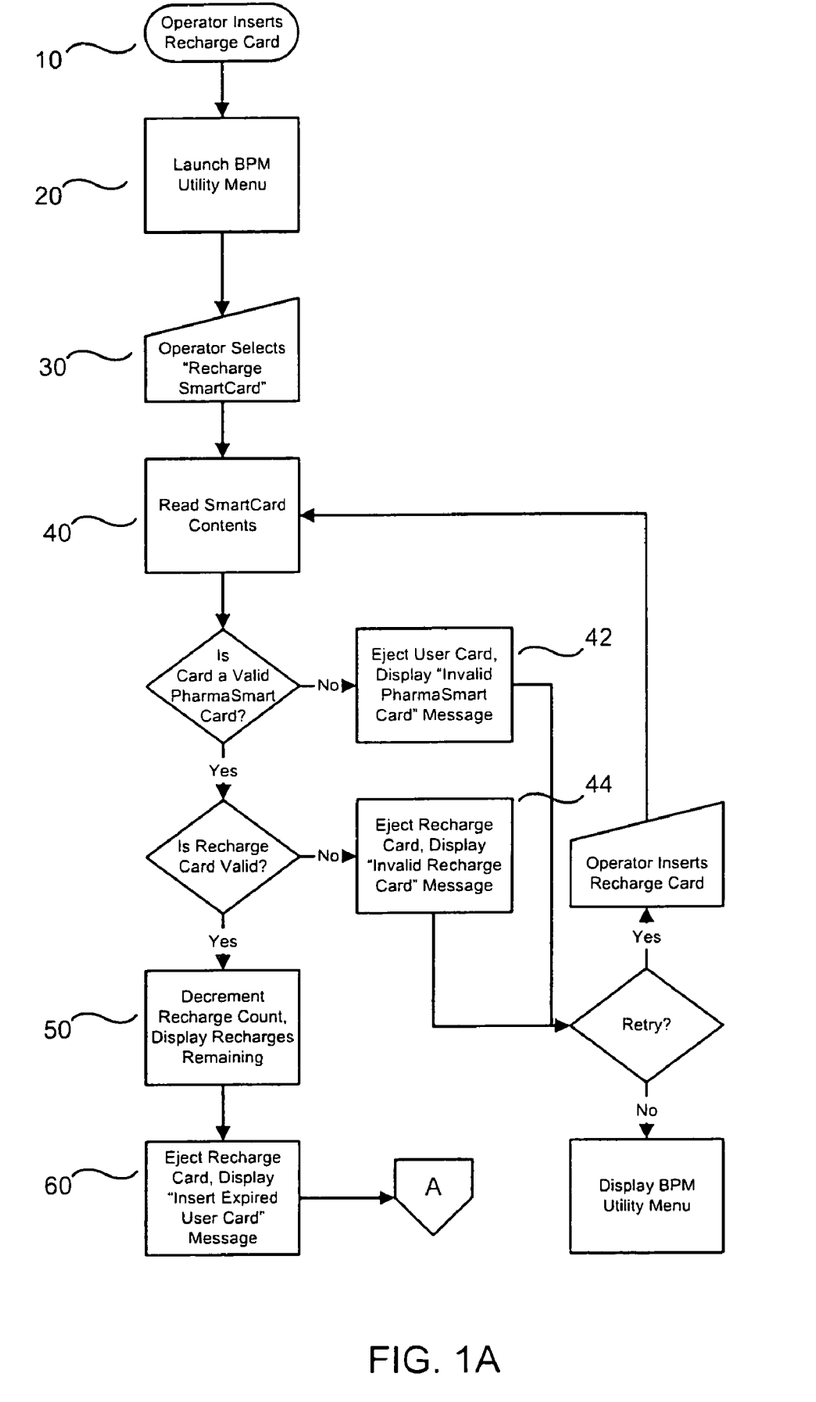
FIG. 1A shows the processing flow of steps for updating a Recharge Card using a single-port card reader.
Figure 1B:
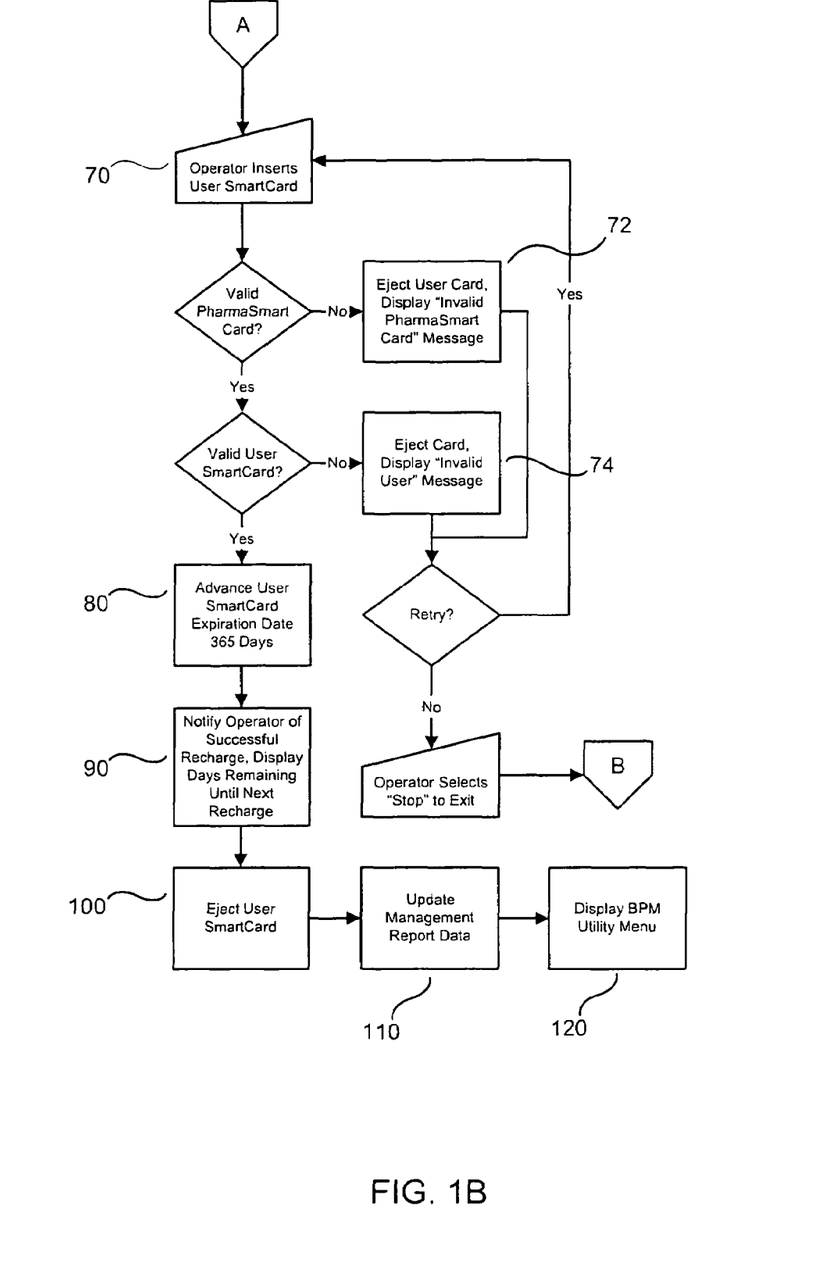
FIG. 1B shows the processing flow of steps for recharging a User Smart Card using a single-port card reader.
Figure 1C:
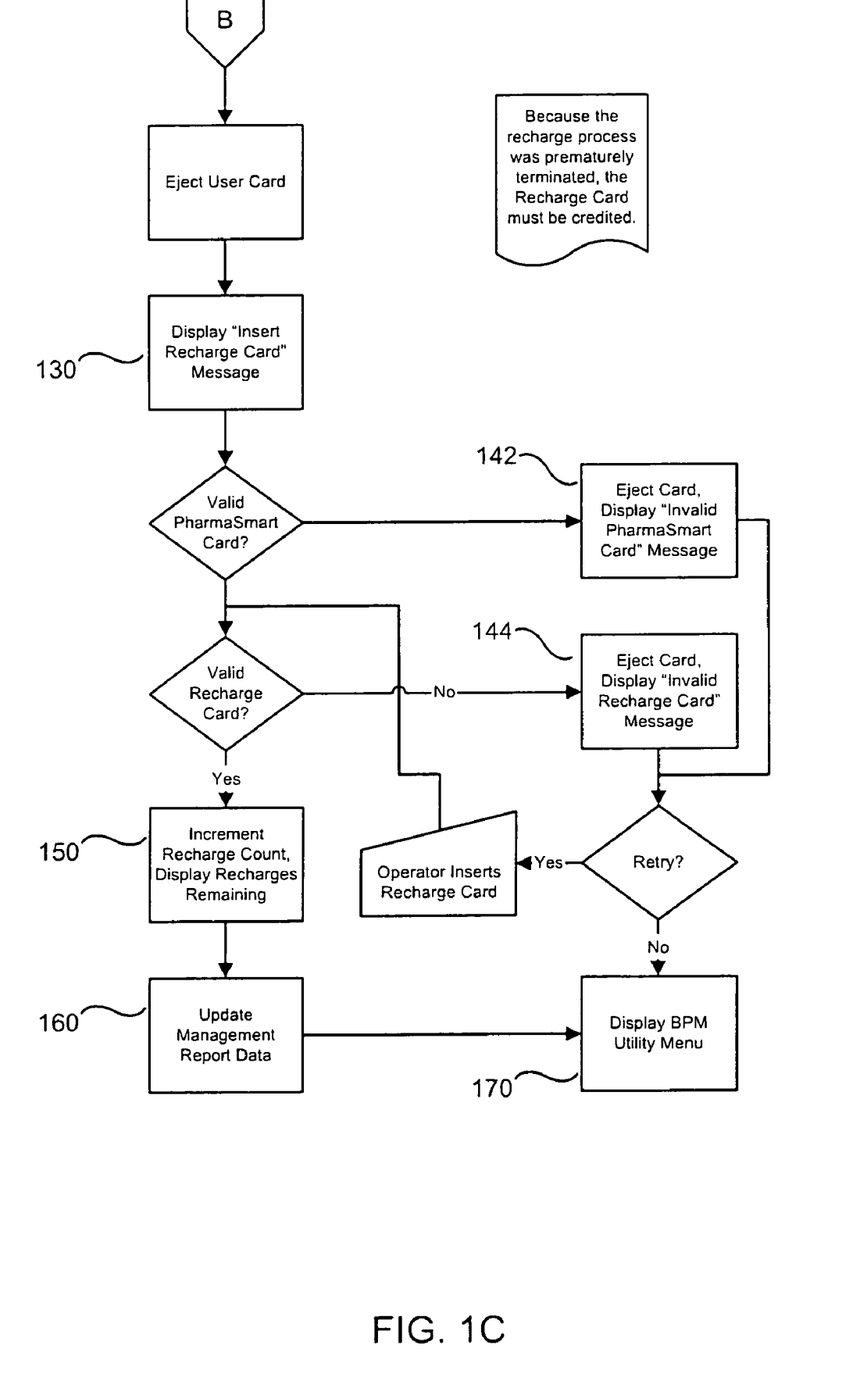
FIG. 1C shows the processing flow of steps for correcting the Recharge Count on a Recharge Card using a single-port card reader.
Figure 3A:
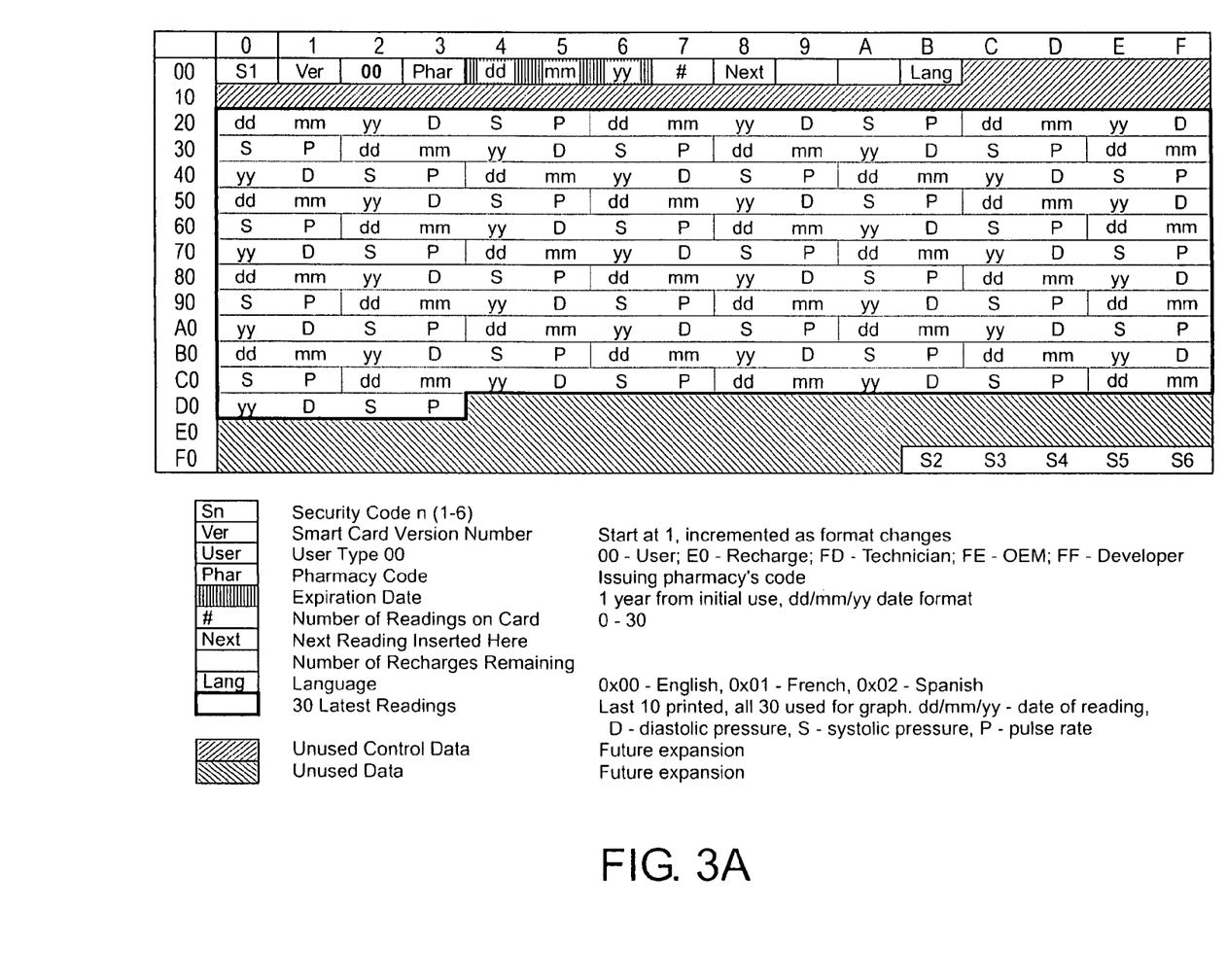
FIG. 3A shows the format of the data stored on the User Smart Card prior to encryption. A memory map of the encrypted card is not shown as the encryption techniques are well known in the art.

FIGS. 1A through 1C show a combined flow chart presenting specific software design and operational details of the Smart Card recharge process as performed using a single-port card reader. There are three overall parts of the recharge process: 1) updating the Recharge Card, 2) updating the User Smart Card, and 3) restoring the Recharge Card to an earlier state when a User Smart Card update has not been completed. FIG. 1A shows the basic steps of the updating of a Recharge Card. Refer to FIG. 3A for the data memory map for the data fields stored on the User Smart Card (User Type '00') and to FIG. 3B for the data fields stored on the Recharge Card (User Type 'E0').

1. The operator inserts (10) the Recharge Card in the card reader.
2. The system presents (20) the BPM utility menu to the operator.
3. The operator selects (30) the "Recharge Smart Card" option from the menu.
4. The system reads (40) the Recharge Card contents. If the card is not a valid PharmaSmart card of any type, the system displays (42) a message to that effect and prompts the user to use a PharmaSmart Recharge card.
5. If the card is a valid PharmaSmart card but not a Recharge Card, the system displays (44) a message to that effect and prompts the user to use a PharmaSmart Recharge card.
6. If the card is a valid PharmaSmart Recharge Card, the system decrements (50) the card's Recharge Count, and displays the number of recharges remaining on the card.
7. The system ejects the Recharge Card and prompts (60) the operator to insert the User Smart Card.

Once the Recharge Smart Card is decremented one credit, the User Smart Card updating process begins. See FIG. 1B for the steps:

1. The operator inserts (70) the User Smart Card.
2. If the card is not a valid PharmaSmart card of any type, the system displays (72) a message to that effect and prompts the user to use a PharmaSmart user Smart Card.
3. If the card is a valid PharmaSmart card but not a User Smart Card, the system displays (74) a message to that effect and prompts the user to use a PharmaSmart User Smart Card.
4. If the card is a valid PharmaSmart User Smart Card, the system advances (80) the card's Expiration Date by 365 days, or if the Expiration Date has passed, sets a new Expiration Date 365 days from the User Smart Card's update.
5. The system notifies (90) the operator of the successful update and displays the total number of days until the User Smart Card will require another recharge.
6. The system ejects (100) the User Smart Card.
7. The system updates (110) its management report data.
8. The system displays (120) the BPM Utility Menu.

During the User Smart Card update, the operator may decide that the recharge process cannot be completed. If the process is not completed, the Recharge Card and the User Smart Card are left in states that are mutually inconsistent. The Recharge Card indicates that a recharge has been done, while the User Smart Card has not been recharged. Consequently, the inconsistency should be corrected. The Recharge Card should be incremented one Recharge Credit.

See FIG. 1C. The steps:

1. The system prompts (130) the operator to insert the Recharge Card.
2. The system reads the Recharge Card contents. If the card is not a valid PharmaSmart card of any type, the system displays (142) a message to that effect and prompts the operator to use a PharmaSmart Recharge card.
3. If the card is a valid PharmaSmart card but not a Recharge Card, the system displays (144) a message to that effect and prompts the operator to use a PharmaSmart Recharge card.
4. If the card is a valid PharmaSmart Recharge Card, the system increments (150) the card's Recharge Credits by one credit, and displays the number of Recharge Credits remaining on the card.
5. The system updates (160) its management report data.
6. The system displays (170) the BPM Utility Menu.

Figure 2A:
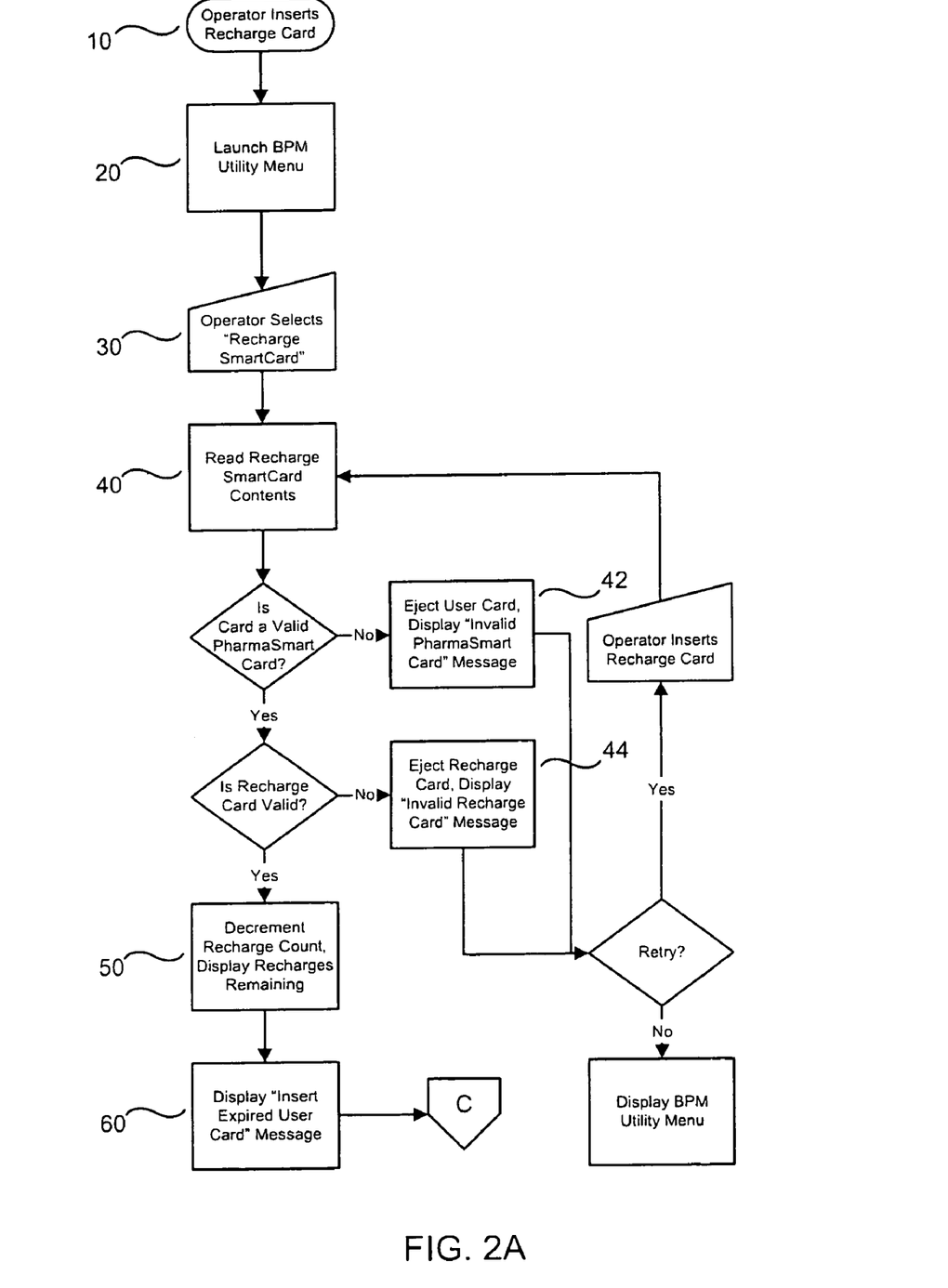
FIG. 2A shows the processing flow of steps for updating a Recharge Card using a dual-port card reader.
Figure 2B:
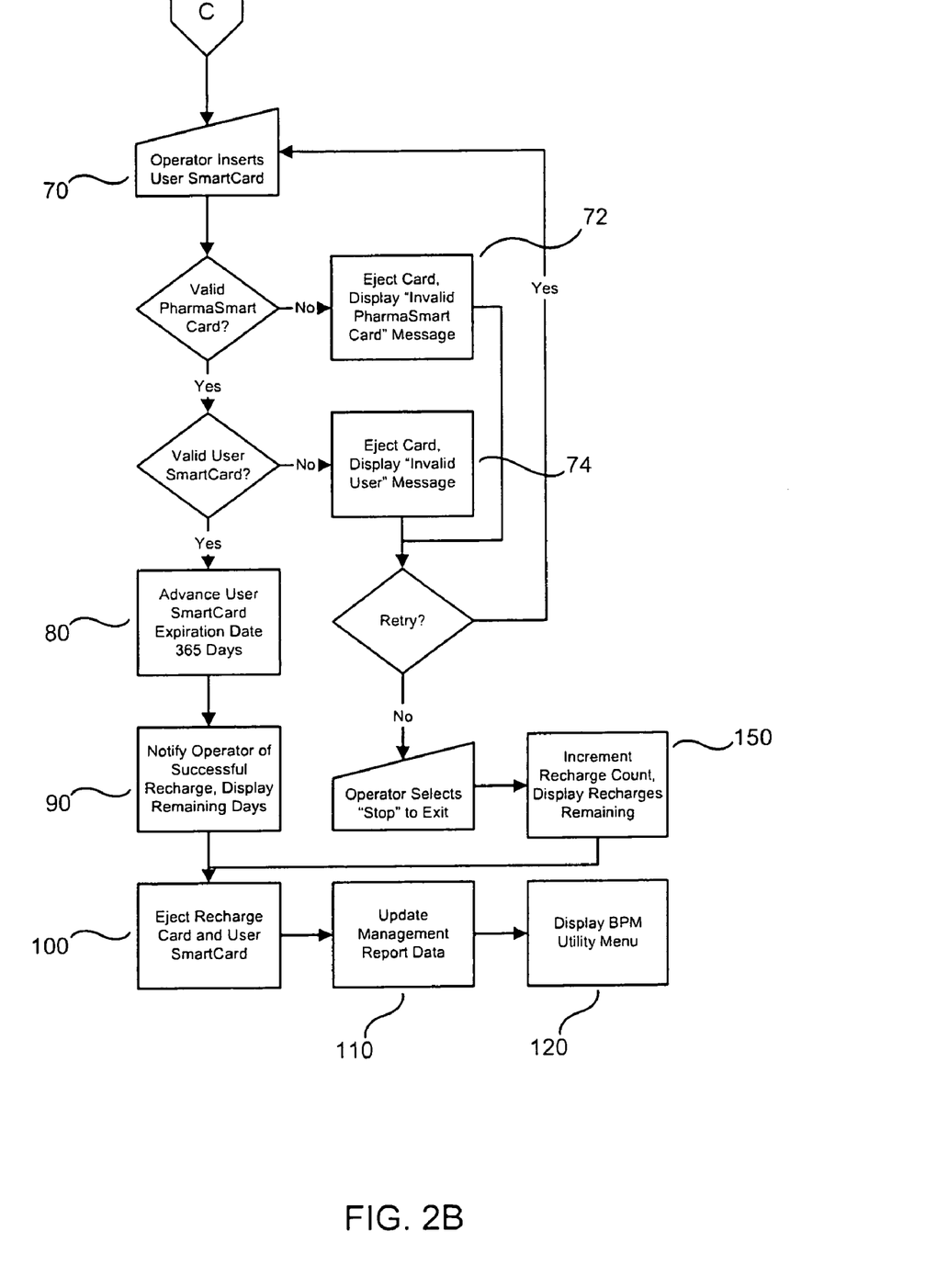
FIG. 2B shows the processing flow of steps for recharging a User Smart Card and correcting the Recharge Count on a Recharge Card using a dual-port card reader.

In an alternative embodiment of the system, a dual-port card reader allows the Recharge Card to remain accessible to the system while the User Smart Card is being updated. In this alternative dual-port embodiment, Step 4 of FIG. 1C is done as part of the process of FIG. 1A after the operator has interrupted the User Smart Card update, and the entire process is simplified as shown in FIGS. 2A and 2B. This alternative dual-port embodiment, while more expensive in hardware terms, has the advantage of eliminating all manual steps for correcting the inconsistency between the Recharge Card and the User Smart Card.

FIG. 2A shows the basic steps of the updating of a Recharge Card:

1. The operator inserts (10) the Recharge Card in the Recharge card reader slot.
2. The system presents (20) the BPM utility menu to the operator.
3. The operator selects (30) the "Recharge Smart Card" option from the menu.
4. The system reads (40) the Recharge Card contents. If the card is not a valid PharmaSmart card of any type, the system displays (42) a message to that effect and prompts the user to use a PharmaSmart Recharge card.
8. If the card is a valid PharmaSmart card but not a Recharge Card, the system displays (44) a message to that effect and prompts the user to use a PharmaSmart Recharge card.
9. If the card is a valid PharmaSmart Recharge Card, the system decrements (50) the card's Recharge Count, and displays the number of recharges remaining on the card.
10. The system prompts (60) the operator to insert the expired User Smart Card in the User Smart Card card reader slot.

Once the Recharge Smart Card is updated, the User Smart Card updating process begins. See FIG. 2B for the steps:
1. The operator inserts (70) the User Smart Card in the User Smart Card reader slot.
2. If the card is not a valid PharmaSmart card of any type, the system displays (72) a message to that effect and prompts the user to use a PharmaSmart user card.
3. If the card is a valid PharmaSmart card but not a User Smart Card, the system displays (74) a message to that effect and prompts the user to use a PharmaSmart User Smartcard.
4. If the card is a valid PharmaSmart User Smart Card, the system advances (80) the card's Expiration Date by 365 days, or if the Expiration Date has passed, sets a new Expiration date 365 days from the User Smart Card's update.
5. If the operator has interrupted the User Smart Card update process without change to the User Smart Card's Expiration Date, the system increments (150) the Recharge Card's Recharge Count, displays the number of recharges remaining on the card.
6. If the operator has completed the User Smart Card update process successfully, the system notifies (90) the operator of the successful update and displays the new expiration date placed on the card.
7. The system ejects (100) the User Smart Card.
8. The system ejects (100) the Recharge Card
9. The system updates (110) its management report data.
10. The system displays (120) the BPM Utility Menu.

Regarding Step 2. identifying a valid PharmaSmart card, the format defined in FIG. 3 contains values in 'Security Code', 'Smart Card Version Number', 'User Type', 'Pharmacy Code', and 'Expiration Date' that may be used in combination in ways well-known in the art to identify the card as a valid PharmaSmart card.

Regarding Step 3. distinguishing between the Recharge Card and the User Smart Card, the formats of the Recharge Card and the User Smart Card are the same, as shown in FIG. 3, except that the Recharge Card contains an 'E0' code in the User Type field, while the User Smart Card contains a '00' in the User Type field. Also, since the Recharge Card is not used for storing readings, the 'Number of Readings on Card', 'Next Reading Inserted Here', and the '30 Latest Readings' on the Recharge Card will not contain valid data unless such data is added by another application.

Figure 3B:
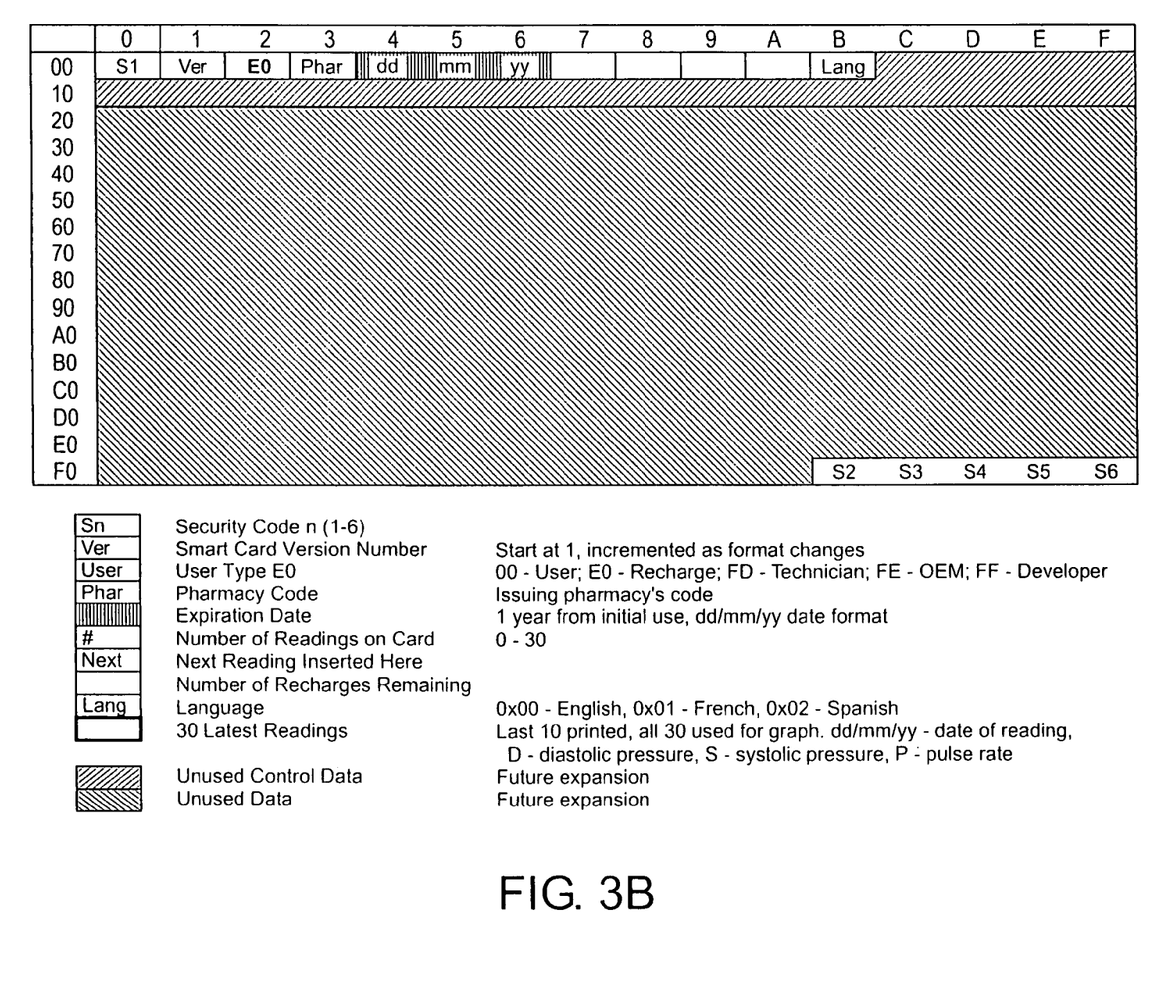
FIG. 3B shows the format of the data stored on the Recharge Card.

See FIGS. 3A and 3B. The User Type field may contain codes that identify other special-purpose card formats as needed for conventional technical and developmental purposes. FIG. 3A shows a map of the memory card. Such cards may be used in the invention but they do not provide security for the data on the card. But they are less expensive than the more secure Smart Cards and can store the same user data that is stored on a Smart Card.

In a general embodiment providing for storage and analysis of non-invasive physiological test data and other medical monitoring information, the invention's User Smart Card records values from automated equipment for reading blood glucose level, blood cholesterol level, or other testable medical parameter values. The range of testable medical parameter values expands constantly as new technologies enable rapid, reliable, low-powered monitoring techniques to be packaged and made available to an End User.

The User Smart Card records the non-invasive physiological test data that the user took over the course of a year. The user can use the User Smart Card to access this entire history at any Location, and print out the most recent 10 entries or all of them. The average of the printed entries is given with the printout. The date of each reading is also recorded on the User Smart Card and printed alongside each entry, allowing the user or a physician to identify trends in the data. Additionally, at the user's request, the data from the User Smart Card can be loaded into the computer system of a pharmacy or doctor's office, allowing health care workers quick access to the user's non-invasive physiological test data.

At a Location, the user can print out the entire history of non-invasive physiological test data stored on the user Smart Card. Additionally, at a pharmacy or physician's office this data can be submitted for a consultation on the patient's condition. When the User Smart Card is recharged, an option is given to allow the user to submit his data to a pharmacy for a consultation.

Tests now performed in a laboratory, such as blood enzyme levels for such critical markers as creatine phosphokinase (CPK), will eventually be capable of being performed properly and inexpensively in a manner similar to that now used for blood pressure monitoring. Furthermore, evaluations requiring significant analysis and processing of data, such as the classification of cardiac arrhythmias requiring medical attention, may become capable of being performed in a consumer setting as well.

Finally, numerous drugs, such as the COX-2 inhibitors, can produce varied deleterious effects on small subsets of their users. The monitoring of blood markers for adverse or allergic reactions to such drugs presents another field of application for the present invention.

To record the values captured, the invention substitutes different value sets and ranges for different types of reading and different sensitivity requirements. For example, readings of blood glucose levels when fasting range from the 60-100 range (excellent) to above 180 (poor), but after a meal the range rises so that the 110-140 range represents an excellent level, while above 220 represents a poor level of blood glucose (source of values: University of Massachusetts Medical School Web page concerning self-monitoring of blood glucose levels using the lancet). Ranges for different classes of monitored values are represented in the invention using range classifications, biasing of values, elimination of non-significant digits of precision, and other techniques well-known in the art for compressing data values for storage in limited memory space.

In a secure embodiment, the invention incorporates conventional anti-tampering hardware and software components in the User Smart Card and the Recharge Card to prevent an End User, a Location employee, or a thief from using a conventional standalone card reader to alter the contents of the User Smart Card or the Recharge Card.

In the secure embodiment, the invention applies encryption to the contents of the card, rendering the contents of the card unreadable by any process except the decryption of the encrypted values. The Location employee (for the Recharge Card) or the End User (for the User Smart Card) reads and updates the card's contents by furnishing the decryption key for the card. The specific encryption techniques used are well-known in the art and so are not described here.

Any attempt to read the card's contents using a conventional standalone card reader triggers the execution of software which breaks open one or more fuses on the card, rendering the card useless. While such measures do not prevent fraudulent misuse of the card, they make such misuse considerably more difficult.

The operation, contents, encryption, and decryptions of the invention's Recharge Card are the same for all classes of data to be collected.

The invention offers additional embodiments usable in non-medical contexts for any application that gathers, stores, and recalls a limited number of data values on a rechargeable basis as described hereinabove. Two such applications are:

1. Transit systems, wherein the invention charges a User Smart Card with travel credit increments deductible by the user at entry into each stage of a journey on a transit system using the invention. At each stage of the journey, the invention notes the time and location of the user's entry for travel, and deducts one or more credit increments as appropriate for the stage on which the user is embarking. The user may afterwards obtain from the Smart Card a record of travel for business or evidentiary reasons.

2. Libraries and lending systems, wherein the invention charges a User Smart Card with lending credit increments deductible by the user when borrowing a book, film, music score, or other item of rental or lease goods or equipment. Different items borrowed may result in different numbers of credit increments being deducted. The invention stores the time and date of lending or rental and the time and date of return of the item on the User Smart Card.

What is claimed is:

1. An apparatus for recording and tracking non-invasive physiological test data comprising:
   a machine for automatically detecting non-invasive physiological test data of an individual;
   means for recording the detected non-invasive physiological test data on a first transportable device adapted to receive and hold non-invasive physiological test data;
   means for recording the date of each recording of non-invasive physiological test data on the first transportable device;
   means for deactivating the first transportable device after a first predetermined number of readings, after a first predetermined duration, or both; and
   means for reactivating the first transportable device to store a second predetermined number of readings, a second predetermined duration, or both.

2. The apparatus of claim 1 further comprising:
   means for preventing access to or alteration of any component of the records of non-invasive physiological test data.

3. The apparatus of claim 2 wherein the means for preventing access to or alteration of any component of the records of non-invasive physiological test data further comprises a means for encryption of the records of non-invasive physiological test data.

4. The apparatus of claim 2 wherein the means for preventing access to or alteration of any component of the records of non-invasive physiological test data further comprises a means for decryption of the records of non-invasive physiological test data.

5. The apparatus of claim 2 wherein the means for preventing access to or alteration of any component of the records of non-invasive physiological test data further comprises a means for destroying the records of non-invasive physiological test data.

6. The apparatus of claim 1 further comprising:
   means for accessing and printing a hard copy of the data contained on the first transportable device.

7. The apparatus of claim 6 wherein the means for accessing and printing a hard copy of the data contained on the first transportable device further comprises:
   a means for accessing data entries contained on the first transportable device alongside the dates the data entries were recorded;
   means for selecting a set of data entries, taking an average of the set of data entries, and displaying or printing the set of data entries including the date the entries were made and their average.

8. The apparatus of claim 7 wherein the selected data entries comprise the last ten entries.

9. The apparatus of claim 7 wherein the selected data entries comprise all the data entries on the card.

10. The apparatus of claim 7 further comprising:
    a means for uploading the data entries onto a computer.

11. The apparatus of claim 1 wherein the means for recording the detected non-invasive physiological test data and the date of each recording on a first transportable device further comprises a first reading and writing device.

12. The apparatus of claim 11 wherein the first reading and writing device further comprises a first electronic smart card reading and writing device.

13. The apparatus of claim 11 wherein the first reading and writing device further comprises a first flash memory reading and writing device.

14. The apparatus of claim 11 wherein the first reading and writing device further comprises a first optical memory reading and writing device.

15. The apparatus of claim 11 wherein the first reading and writing device further comprises a first magneto-optical memory reading and writing device.

16. The apparatus of claim 1 wherein the detected non-invasive physiological test data further comprise one or more of the group consisting of:
    the systolic blood pressure of the individual;
    the diastolic blood pressure of the individual;
    the pulse rate of the individual;
    the respiration rate of the individual;
    the blood oxygen level of the individual;
    the blood glucose level of the individual;
    the blood cholesterol level of the individual;
    one or more blood enzyme levels of the individual;
    indications and a log of one or more classes of cardiac arrythmias of the individual;
    the weight of the individual;
    the percent body fat of the individual; and
    the bone density of the individual.

17. An apparatus for recording and tracking non-invasive physiological test data comprising:
    a machine for automatically detecting non-invasive physiological test data of an individual;
    means for recording the detected non-invasive physiological test data on a first transportable device adapted to receive and hold non-invasive physiological test data;
    means for recording the date of each recording of non-invasive physiological test data on the first transportable device;
    means for deactivating the first transportable device after a first predetermined number of readings, after a first predetermined duration, or both; and
    means for reactivating the first transportable device to store a second predetermined number of readings, a second predetermined duration, or both;
    wherein the means for deactivating the first transportable device after a first predetermined number of readings, after a first predetermined duration, or both further comprises:

a machine-readable and machine-writable recording of expiration date information, stored on the first transportable device;

a source of current date information not stored on the first transportable device;

a software program for comparing the current date information with the expiration date information; and the results of a comparison between the expiration date information and the current date information.

18. The apparatus of claim 17 wherein the first transportable device comprises an electronic smart card.

19. The apparatus of claim 17 wherein the first transportable device comprises a flash memory card.

20. The apparatus of claim 17 wherein the first transportable device comprises an optical memory device.

21. The apparatus of claim 17 wherein the first transportable device comprises a magneto-optical memory device.

22. An apparatus for recording and tracking non-invasive physiological test data comprising:

a machine for automatically detecting non-invasive physiological test data of an individual;

means for recording the detected non-invasive physiological test data on a first transportable device adapted to receive and hold non-invasive physiological test data;

means for recording the date of each recording of non-invasive physiological test data on the first transportable device;

means for deactivating the first transportable device after a first predetermined number of readings, after a first predetermined duration, or both; and means for reactivating the first transportable device to store a second predetermined number of readings, a second predetermined duration, or both;

wherein the means for reactivating the first transportable device further comprises:

a second transportable device for limiting the number of reactivating operations performed on one or more first transportable devices;

a machine-readable and machine-writable recording of the number of reactivating operations, stored on the second transportable device and specifying the number of reactivating operations remaining to be performed;

a software program for decrementing the number of reactivating operations remaining to be performed;

the results of a comparison between the number of reactivating operations remaining to be performed and zero; and a software program for resetting the expiration date information stored on the first transportable device.

23. The apparatus of claim 22 wherein the second transportable device comprises an electronic smart card.

24. The apparatus of claim 22 wherein the second transportable device comprises a flash memory card.

25. The apparatus of claim 22 wherein the second transportable device comprises an optical memory device.

26. The apparatus of claim 22 wherein the second transportable device comprises a magneto-optical memory device.

27. The apparatus of claim 22 wherein the means for reactivating the first transportable device further comprises a second reading and writing device.

28. The apparatus of claim 27 wherein the first reading and writing device further comprises a second electronic smart card reading and writing device.

29. The apparatus of claim 27 wherein the first reading and writing device further comprises a second flash memory reading and writing device.

30. The apparatus of claim 27 wherein the first reading and writing device further comprises a second optical memory reading and writing device.

31. The apparatus of claim 27 wherein the first reading and writing device further comprises a magneto-optical memory reading and writing device.

32. A process for recording and tracking non-invasive physiological test data comprising the steps of:

detecting the non-invasive physiological test data of an individual;

recording the detected non-invasive physiological test data on a first transportable device adapted to receive and hold non-invasive physiological test data;

recording the date of each recording of non-invasive physiological test data on the first transportable device;

limiting the duration, number of recordings made, or both on the first transportable device to a first period of time;

deactivating the first transportable device after the first period of time; and reactivating the first transportable device to store a second period of time comprising a duration, number of recordings made, or both.

33. The process of claim 32, wherein the step of detecting the non-invasive physiological test data of an individual further comprises the steps of:

the systolic blood pressure of the individual;

the diastolic blood pressure of the individual;

the pulse rate of the individual;

the respiration rate of the individual;

the blood oxygen level of the individual;

the blood glucose level of the individual;

the blood cholesterol level of the individual;

one or more blood enzyme levels of the individual;

indications and a log of one or more classes of cardiac arrythmias of the individual;

the weight of the individual;

the percent body fat of the individual; and the bone density of the individual.

34. The process of claim 32, wherein the step of limiting the duration and number of recordings made on the first transportable device to a first period of time further comprises the steps of:

at the time of reactivating of the first transportable device, writing an expiration date of the first period of time onto the first transportable device;

at the time of routine use by a user, reading the expiration date of the first period of time stored on the first transportable device;

at the time of routine use by a user, comparing the expiration date to the current date;

when the expiration date has been passed at the time of routine use by a user, notifying the user of the first transportable device that said device requires reactivating.

35. A process for recording and tracking non-invasive physiological test data comprising the steps of:

detecting the non-invasive physiological test data of an individual;

recording the detected non-invasive physiological test data on a first transportable device adapted to receive and hold non-invasive physiological test data;

recording the date of each recording of non-invasive physiological test data on the first transportable device;

deactivating the first transportable device after a first predetermined number of readings, after a first predetermined duration, or both; and reactivating the first transportable device to store a second predetermined number of readings, a second predetermined duration, or both;

wherein the step of recording the detected non-invasive physiological test data on a first transportable device further comprises the steps of:

at the time of routine use by a user, reading the expiration date on the first transportable device;

at the time of routine use by a user, comparing the expiration date to the current date; and when the expiration date has not been passed at the time of routine use by a user, recording the detected non-invasive physiological test data on the first transportable device.

36. A process for recording and tracking non-invasive physiological test data comprising the steps of:

detecting the non-invasive physiological test data of an individual;

recording the detected non-invasive physiological test data on a first transportable device adapted to receive and hold non-invasive physiological test data;

recording the date of each recording of non-invasive physiological test data on the first transportable device;

deactivating the first transportable device after a first predetermined number of readings, after a first predetermined duration, or both; and reactivating the first transportable device to store a second predetermined number of readings, a second predetermined duration, or both;

wherein the step of reactivating the first transportable device further comprises the steps of:

at the time of authorization of additional reactivation operations for one or more first transportable devices, writing a count of reactivation operations available onto a second transportable device;

at the time of reactivation of the first transportable device, reading a count of reactivation operations available from the second transportable device;

at the time of reactivation of the first transportable device, decrementing the count of reactivation operations available;

when the count of reactivation operations available has reached zero, notifying the operator that the second transportable device requires authorization of further reactivation operations; and when the count of reactivation operations available has not reached zero, writing the expiration date of the second period of time onto the first transportable device.

37. An apparatus for recording and tracking usage information comprising:

a machine for automatically detecting parameters of usage of a service, resource or object;

means for recording parameters of the detected usage on a first transportable device adapted to receive and hold usage data;

means for limiting the duration, number of recordings made, or both on the first transportable device to a first period of time, wherein the first transportable device ceases to record non-invasive physiological test data once a predetermined limit for the first period of time is exceeded;

means for reactivating the first transportable device to extend the first period of time to a second period of time;

means for limiting the duration, number of recordings made on the first transportable device, or combination thereof to a second period of time;

means for preventing access to or alteration of any component of the records of usage information;

wherein reactivating the first transportable device to extend the first period of time to a second period of time permits continued recording of non-invasive physiological test data until a predetermined limit for the second period of time is reached.

38. The apparatus of claim 37 wherein the parameters of usage comprise the time, date, and location of the usage.

39. The apparatus of claim 37 wherein the service, resource, or object is selected from the list consisting of:

passage on a transit conveyance;

borrowing of a book, recording, or other document; and rental of a piece of equipment.

40. The apparatus of claim 37 wherein the means for preventing access to or alteration of any component of the records of non-invasive physiological test data further comprises a means for encryption of the records of usage information.

41. The apparatus of claim 37 wherein the means for preventing access to or alteration of any component of the records of non-invasive physiological test data further comprises a means for decryption of the records of usage information.

42. The apparatus of claim 37 wherein the means for preventing access to or alteration of any component of the records of non-invasive physiological test data further comprises a means for destroying the records of usage information.

* * * * *